(12) United States Patent
Skwarek et al.

(10) Patent No.: US 7,437,194 B2
(45) Date of Patent: Oct. 14, 2008

(54) STIMULATING THE PROSTATE GLAND

(75) Inventors: Thomas R. Skwarek, Shoreview, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 446 days.

(21) Appl. No.: 10/698,881

(22) Filed: Oct. 31, 2003

(65) Prior Publication Data
US 2005/0096709 A1  May 5, 2005

(51) Int. Cl.
*A61N 1/00* (2006.01)
(52) U.S. Cl. ....................................................... 607/39
(58) Field of Classification Search .................... 607/39
See application file for complete search history.

(56) References Cited

U.S. PATENT DOCUMENTS

| | | | | |
|---|---|---|---|---|
| 4,585,005 | A | * | 4/1986 | Lue et al. ........................ 607/39 |
| 4,663,102 | A | * | 5/1987 | Brenman et al. ............. 264/222 |
| 4,771,779 | A | | 9/1988 | Tanagho et al. |
| 4,858,005 | A | | 8/1989 | Lodge |
| 5,199,430 | A | | 4/1993 | Fang et al. |
| 5,220,927 | A | * | 6/1993 | Astrahan et al. ............. 607/156 |
| 5,454,840 | A | * | 10/1995 | Krakovsky et al. ............. 607/39 |
| 5,462,644 | A | * | 10/1995 | Woodson ...................... 205/701 |
| 5,690,691 | A | | 11/1997 | Chen et al. |
| 5,775,331 | A | * | 7/1998 | Raymond et al. ............ 600/554 |
| 6,061,596 | A | | 5/2000 | Richmond et al. |
| 6,169,924 | B1 | | 1/2001 | Meloy et al. |
| 6,179,831 | B1 | * | 1/2001 | Bliweis ........................ 606/21 |
| 6,185,452 | B1 | | 2/2001 | Schulman et al. |
| 6,231,591 | B1 | | 5/2001 | Desai |
| 6,241,701 | B1 | * | 6/2001 | Hofmann ....................... 604/21 |
| 6,241,702 | B1 | | 6/2001 | Lundquist et al. |
| 6,271,211 | B1 | * | 8/2001 | Christ et al. .................... 514/44 |
| 6,296,847 | B1 | * | 10/2001 | Gokcen et al. ............. 424/94.2 |
| 6,365,164 | B1 | | 4/2002 | Schmidt |
| 6,402,742 | B1 | * | 6/2002 | Blewett et al. ................ 606/34 |
| 6,449,512 | B1 | | 9/2002 | Boveja |
| 6,507,755 | B1 | | 1/2003 | Gozani et al. |
| 6,537,272 | B2 | | 3/2003 | Christopherson et al. |
| 6,551,300 | B1 | | 4/2003 | McGaffigan |

(Continued)

OTHER PUBLICATIONS

Gacci, M, R Bartoletti, S Figlioli, E Sarti, B Eisner, V Boddi, and M Rizzo. "Urinary Symptoms, Qulaity of Life Sexual Function in Patients with Benign Prostatic Hypertrophy Before and After Prostatectomy: a Prospective Study." BJU International 91(3) (Feb. 2003): 197-200. Abstract.*

(Continued)

*Primary Examiner*—George Manuel
*Assistant Examiner*—Christopher A Flory
(74) *Attorney, Agent, or Firm*—Shumaker & Sieffert, PA

(57) ABSTRACT

The invention is directed to techniques for providing electrical stimulation to the prostate gland of a patient. In particular, various techniques are described for providing such stimulation in order to treat sexual dysfunction, benign prostatic hyperplasia (BPH), or other disorders. In some embodiments, the stimulation may be provided to the prostate gland to cause erection or ejaculation in order to treat various sexual dysfunctions. In other embodiments, the stimulation may comprise a training sequence of pulses selected to train and modify the cellular structure of the prostate gland in order to treat BPH or similar prostate disorders.

14 Claims, 5 Drawing Sheets

U.S. PATENT DOCUMENTS

| | | | |
|---|---|---|---|
| 6,571,128 | B2 | 5/2003 | Lebel et al. |
| 6,650,943 | B1 | 11/2003 | Whitehurst et al. |
| 6,735,474 | B1 | 5/2004 | Loeb et al. |
| 6,852,323 | B2 | 2/2005 | Lue et al. |
| 6,862,479 | B1 | 3/2005 | Whitehurst et al. |
| 6,875,176 | B2 * | 4/2005 | Mourad et al. ............... 600/442 |
| 6,885,895 | B1 * | 4/2005 | Whitehurst et al. ........... 607/39 |
| 6,901,294 | B1 * | 5/2005 | Whitehurst et al. ........... 607/39 |
| 6,907,293 | B2 | 6/2005 | Grill et al. |
| 6,941,171 | B2 * | 9/2005 | Mann et al. .................... 607/39 |
| 6,994,706 | B2 * | 2/2006 | Chornenky et al. ........... 606/41 |
| 7,006,870 | B1 | 2/2006 | Whitehurst et al. |
| 7,054,689 | B1 | 5/2006 | Whitehurst et al. |
| 7,130,697 | B2 * | 10/2006 | Chornenky et al. ......... 607/101 |
| 2001/0025192 | A1 | 9/2001 | Gerber et al. |
| 2002/0025327 | A1 | 2/2002 | Schmidt |
| 2002/0055761 | A1 | 5/2002 | Mann et al. |
| 2002/0147485 | A1 | 10/2002 | Mamo et al. |
| 2002/0183740 | A1 | 12/2002 | Edwards et al. |
| 2003/0045919 | A1 | 3/2003 | Swoyer et al. |
| 2004/0015204 | A1 | 1/2004 | Whitehurst et al. |
| 2004/0019369 | A1 | 1/2004 | Duncan et al. |
| 2004/0049240 | A1 * | 3/2004 | Gerber et al. .................. 607/40 |
| 2004/0153127 | A1 | 8/2004 | Gordon et al. |
| 2004/0236381 | A1 | 11/2004 | Dinsmoor et al. |
| 2005/0070969 | A1 * | 3/2005 | Gerber ......................... 607/40 |
| 2005/0096709 | A1 | 5/2005 | Skwarek et al. |
| 2005/0113877 | A1 * | 5/2005 | Spinelli et al. ................ 607/39 |
| 2005/0113887 | A1 * | 5/2005 | Bauhahn et al. ............... 607/61 |
| 2005/0187427 | A1 * | 8/2005 | Connors et al. ............... 600/29 |
| 2005/0282745 | A1 * | 12/2005 | Siler-Khodr ................. 514/12 |
| 2006/0020297 | A1 | 1/2006 | Gerber et al. |

OTHER PUBLICATIONS

Lukacs, B. "Assessment of Male Sexual Function." Prostate Cancer and Prostatic Diseases 4(S1) (2001): s7-s11. Abstract.*

Schou, J, N R. Holm, and H H. Meyhoff. "Sexual Function in Patients with Symptomatic Benign Prostatic Hyperplasia." Scandinavian Journal of Urology and Nephrology 179 (1996): 119-122. Abstract.*

Carbone, Dj, and S Hodges. "Medical Therapy for Benign Prostatic Hyperplasia: Sexual Dysfunction and Impact on Quality of Life." International Journal of Impotence Research 15(4) (Aug. 2003): 299-306. Abstract.*

Ibrahim, A I., E M. El-Malik, G Ismail, M Rashid, and A B. Al Zahrani. "Risk Factors Associated with Sexual Dysfunction After Transurethral Resection of the Prostate." Annals of Saudi Medicine 22(1-2) (2002): 8-12. Abstract.*

"Treatment Of Sexual Dysfunction By Neurostimulation", filed May 19, 2003, U.S. Appl. No. 10/441,784.

Berman, J. et al., "Female Sexual Function and Dysfunction," Office of Education HO255 IC, American Urological Association, Inc., Orlando, 97th Annual Meeting, May 25-30, 2002, 34 pages.

Brindley, G.S., "Sacral root and hypogastric plexus stimulators and what these models tell us about autonomic actions on the bladder and urethra," Clinical Science, vol. 70 (Suppl. 14), pp. 41-44 (1986).

Gerstenberg et al.,"Erection and Ejaculation in Man. Assessment of the Electromyographic Activity of the bulbocavernosus and Ischiocavernosus Muscles," Br. J. Urol. 65, pp. 395-402 (1990).

* cited by examiner

STIMULATING THE PROSTATE GLAND

FIELD OF THE INVENTION

The invention relates generally to medical treatment of the prostate gland.

BACKGROUND

Benign prostatic hyperplasia (BPH) is a prostate disorder that is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling.

One common surgical procedure used for treating BPH is transurethral needle ablation (TUNA). The TUNA technique involves transurethral delivery of an electrically conductive ablation needle to the prostate site. The electrically conductive ablation needle penetrates the prostate gland in a direction generally perpendicular to the urethral wall, and delivers electrical current to ablate prostate tissue. The electrical current heats tissue surrounding the ablation needle tip to destroy prostate cells, and thereby create a lesion within the prostate gland. The destroyed cells may be absorbed by the body, infiltrated with scar tissue or become non-functional.

U.S. Pat. No. 6,551,300 to McGaffigan discloses a transurethral ablation device that delivers a topically applied anesthetic agent gel to a urethral wall. U.S. Published patent application No. 2002/0183740 to Edwards et al. discloses a transurethral ablation device to ablate prostate tissue via electrically conductive needles. U.S. Pat. No. 6,241,702 to Lundquist et al. describes another transurethral ablation needle device. U.S. Pat. No. 6,231,591 describes instruments for localized delivery of fluids to a portion of body tissue, including the prostate. U.S. Pat. No. 6,537,272 to Christopherson et al. describes creation of a virtual electrode by delivery of a conductive fluid to a tissue site. U.S. Pat. No. 6,365,164 to Schmidt and U.S. Patent publication 2002/0025327 disclose the use of neurotoxin therapy for treatment of urologic and related disorders.

Sexual dysfunction is another common problem experienced by older men. Conventionally, sexual dysfunction is often thought to be influenced by the sacral nerves. For this reason, techniques involving neurostimulation to treat sexual dysfunction have been developed, for example, as described in U.S. Pat. No. 5,454,840 to Krakovsky et al. and U.S. Pat. No. 6,169,924 to Meloy. The Krakovsky patent describes stimulation of the pelvic splanchnic nerve to achieve erection, and stimulation of the pelvic plexus nerves to achieve emission. The Meloy patent describes stimulation of the spinal cord to achieve orgasm. U.S. Published Patent Application No. 20010025192 to Gerber describes implantable leads for sacral nerve electrical stimulation. U.S. Published Patent Application No. 20020055761 to Mann et al. describes delivery of electrical stimulation to treat sexual dysfunction. U.S. Pat. No. 4,585,005 to Lue et al. describes a method and pacemaker for stimulating penile erection.

Table 1 below lists various documents that disclose transurethral ablation techniques for prostate treatment, techniques for neurotoxin delivery to treat urologic disorders, and various techniques for providing neurostimulation to treat sexual dysfunction.

TABLE 1

| Patent Number | Inventors | Title |
|---|---|---|
| 2002/0183740 | Edwards et al. | Medical probe device and method |
| 6,551,300 | McGaffigan | Device and method for delivery of topically applied local anesthetic to wall forming a passage in tissue |
| 6,241,702 | Lundquist et al. | Radio frequency ablation device for treatment of the prostate |
| 6,231,591 | Desai | Method of localized fluid therapy |
| 6,537,272 | Christopherson et al. | Apparatus and method for creating, maintaining, and controlling a virtual electrode used for the ablation of tissue |
| 6,365,164 | Schmidt | Use of neurotoxin therapy for treatment of urologic and related disorders |
| 2002/0025327 | Schmidt | Use of neurotoxin therapy for treatment of urologic and related disorders |
| 5,454,840 | Krakovsky et al. | Potency Package |
| 6,169,924 | Meloy | Spinal Cord Stimulation |
| 20010025192 | Gerber et al. | Single and multi-polar implantable lead for sacral nerve electrical stimulation |
| 20020055761 | Mann et al. | Implantable stimulator systems and methods for treatment of incontinence and pain |
| 4,585,005 | Lue et al | Method and pacemaker for stimulating penile erection |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, some of the devices and methods disclosed in the patents of Table 1 may be modified advantageously in order to exploit techniques of the present invention.

SUMMARY OF THE INVENTION

The invention is directed to techniques for providing electrical stimulation to the prostate gland of a patient. In particular, various techniques are described for providing such stimulation in order to treat sexual dysfunction, benign prostatic hyperplasia (BPH), or other prostate disorders. For example, stimulation may be provided to the prostate gland to cause or prevent erection or ejaculation in order to treat various sexual dysfunctions. In that case, the stimulation may comprise discrete pulses delivered to specific targets of the prostate gland.

In other embodiments, the stimulation may be provided prostate gland in order to treat BPH. In that case, the stimulation may comprise a training sequence of pulses selected to train and modify the cellular structure of the prostate gland. In some cases, drug therapy may be delivered in conjunction with the stimulation to the prostate gland. In those cases, the stimulation may augment or trigger the drug therapy.

The invention has certain objects. That is, various embodiments of the invention provide solutions to one or more problems existing in the prior art with respect to treatment of benign prostatic hyperplasia (BPH) or sexual dysfunction. The problems include, for example, pain and trauma associated with some existing transurethral ablation techniques. In existing techniques for treating BPH, such as the TUNA procedure, electrode needles are deployed into the urethral wall to penetrate prostate tissue to be ablated. The needles deliver energy to ablate prostate tissue and thereby form lesions. Delivery of ablation energy can be traumatic and painful for some patients. In addition, ablation techniques may be difficult to perform for some patients.

Problems with existing techniques for treating sexual dysfunction include the ineffectiveness of such existing techniques for some patients. For example, electrical stimulation to the sacral nerves or other conventional locations may be ineffective in causing erection or ejaculation in some patients.

Various embodiments of the present invention have the object of solving at least one of the foregoing problems. For example, it is an object of the present invention to overcome at least some of the disadvantages of the ablation procedures for treatment of BPH. To that end, it is a further object of the invention to provide an alternative to an ablation procedure for BPH therapy. As another object, the invention may provide BPH therapies that are less painful to the patient.

Another object of the present invention is to overcome at least some of the disadvantages and shortcomings of conventional treatment of sexual dysfunction. To that end, it is a further object of the invention to provide an alternative to conventional neurostimulation techniques used to treat sexual dysfunction. The alternatives described herein may be more effective in treating sexual dysfunction for some patients.

Various embodiments of the invention may possess one or more features capable of fulfilling the objects identified above. In general, the invention provides techniques and devices for delivering electrical stimulation to tissue of the prostate gland of a patient. The stimulation pulses that are delivered may depend on the disorder being treated. For example, stimulation may be provided to the tissue of the prostate gland to cause or prevent erection or ejaculation in order to treat various sexual dysfunctions. In that case, the stimulation may comprise discrete pulses to specific targets of the prostate gland, or a continuous steam of pulses that affect the nervous system proximate to the prostate gland.

In other embodiments, the stimulation may be provided to the prostate gland in order to treat BPH. In that case, the stimulation may comprise a training sequence of pulses selected to train and modify the cellular structure of the prostate gland. For example, a training sequence of pulses delivered over a course of weeks or months may train the prostate gland to become more compliant, thereby alleviating symptoms of BPH. In some cases, drug therapy may be delivered in conjunction with the stimulation to the prostate. In those cases, the stimulation may augment or trigger the drug therapy for treatment of BPH, sexual dysfunction or disorders related to the prostate gland.

In comparison to known implementations of prostate ablation, various embodiments of the present invention may provide one or more advantages. In particular, the invention provides alternatives to an ablation procedure for treatment of BPH or other prostate disorders. For example, delivery of a training sequence of therapeutic pulses to the prostate gland may effectively treat BPH without the pain and trauma associated with some known ablation techniques.

Moreover, in comparison to known techniques for treating sexual dysfunction, the invention can provide significant improvements. For example, the invention may provide alternatives to conventional sacral nerve stimulation for treating sexual dysfunction. Some patients, for example, may be more responsive to prostate stimulation as a sexual dysfunction therapy.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

The invention is directed to techniques for delivering therapeutic stimulation pulses to the prostate gland of a patient via an implantable medical device. In particular, various techniques are described for providing such stimulation in order to treat sexual dysfunction, benign prostatic hyperplasia (BPH), or other prostate or urological disorders. For example, stimulation may be provided to the prostate gland to cause or prevent erection or ejaculation in order to treat various sexual dysfunctions. In that case, the stimulation may comprise discrete pulses delivered to specific targets of the prostate gland. Also, the stimulation may be provided to the prostate gland in order to treat BPH or other urological disorders. In that case, the stimulation may comprise a training sequence of pulses selected to train and modify the cellular structure of the prostate gland. In some cases, drug or genetic therapy may be delivered in conjunction with the stimulation to the prostate. In those cases, the stimulation may augment or trigger the drug or genetic therapy.

Figure 1:
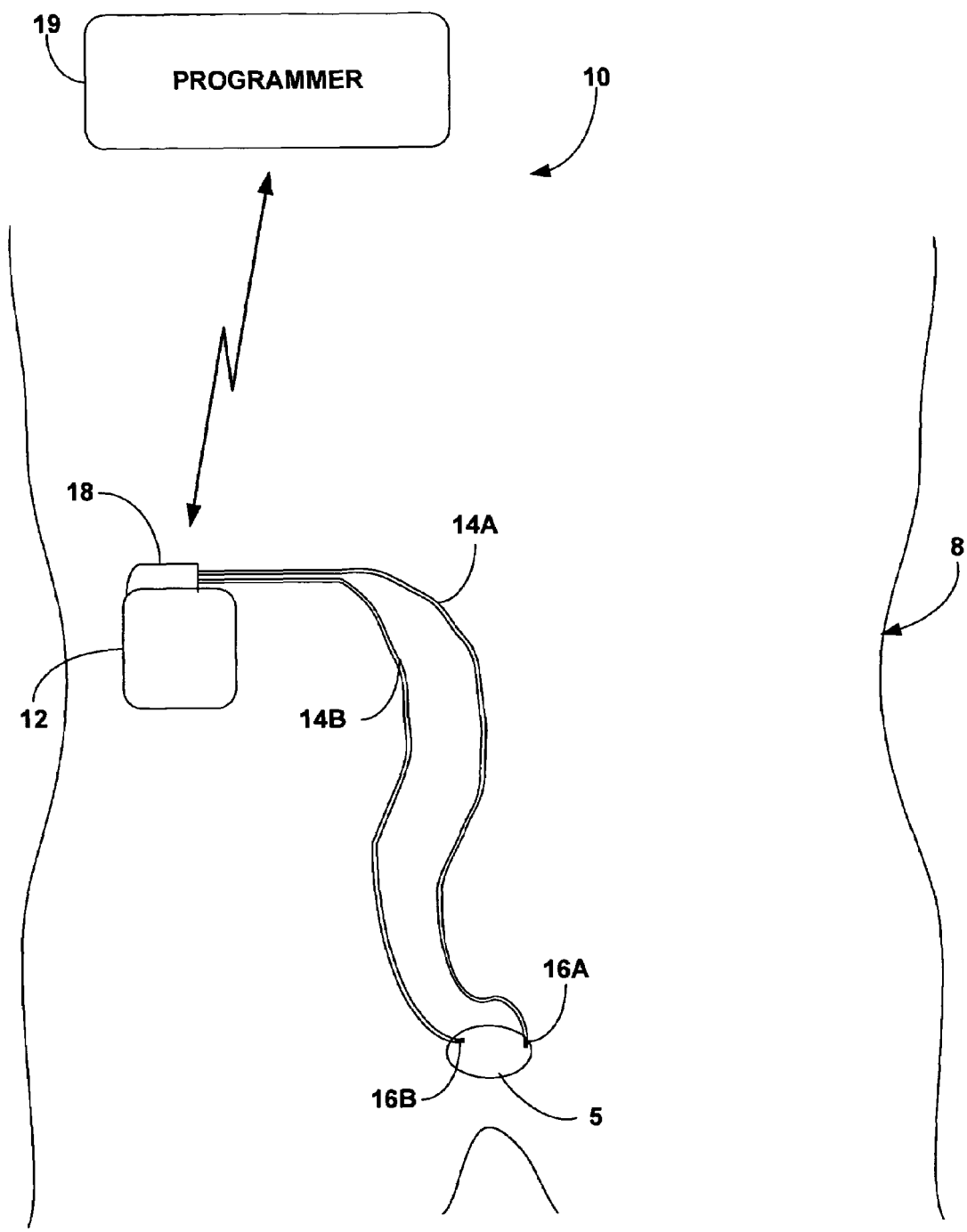
FIG. 1 is a schematic diagram illustrating a system for delivery of therapeutic stimulation pulses to a prostate gland of a patient.

FIG. 1 is a schematic diagram illustrating a system 10 for delivery of therapeutic stimulation pulses to a prostate gland 5 of patient 8. System 10 includes an implantable medical device (IMD) 12 including one or more stimulation leads 14A, 14B implanted within a patient 8. In particular, leads 14 each include one or more electrodes 16A, 16B implanted adjacent prostate gland 5 such that therapeutic stimulation pulses generated by implantable medical device 12 can be delivered through leads 14 to stimulate prostate gland 5 at locations where electrodes 16 are implanted. Leads 14 may comprise monopolar leads, bipolar leads, or may include any number of electrodes. For simplicity, however, monopolar leads are illustrated. If desired, leads 14 may include tissue fixation elements (not shown) to improve fibrous growth about leads 14 in order to anchor electrodes 16 at desired implantation sites. For example, the distal end of leads 14 may includes flanges, tines, a saw-tooth structure, an abrasive material, a beaded coating, rings, or any other material which would allow electrodes 16 to be implanted within prostate gland 5 such that tissue growth of prostate gland 5 anchors electrodes 16 in prostate gland 5. In one example, electrodes 16 comprise fixation coils that can be screwed into prostate gland 5.

Device 12 may comprise a stimulation device similar to those conventionally used for neurostimulation, and typically includes a pulse generator to generate therapeutic stimulation pulses. Device 12 may also include a processor to select or define the pulse sequence and command the pulse generator to generate such a sequence of pulses. In particular, the processor can be programmed to define a sequence desirable for prostate stimulation, as outlined in greater detail below. In any case, device 12 delivers the pulse sequence to prostate gland 5 via leads 14. The proximal ends of leads 14 are coupled to a connector block 18 associated with device 12. Electrodes 16 on distal ends of leads 14 are deployed adjacent prostate gland 5. For example, electrodes 16 may be deployed on or implanted within the cellular muscle tissue of prostate gland 5. As used in this disclosure, the phrase "adjacent the prostate gland" is meant to describe any such implantation location, e.g., on or within the cellular or muscular tissue of prostate gland 5 such that stimulation pulses can be delivered to prostate gland 5.

System 10 also includes a programmer 19 which can be used to program the desirable stimulation pulse sequence to device 12, e.g., via telemetry. Programmer 19 may comprise a physician programmer that allows the physician to define and upload a pulse sequence to device 12 consistent with desirable prostate therapy. Alternatively, programmer 19 may comprise a patient programmer which allows patient 8 to select the timing of therapy, e.g., for sexual dysfunction embodiments. In some cases, different programmers may be used by the physician and the patient to communicate with implantable medical device 12.

Programmer 19 may comprise a handheld computing device that permits a physician, or clinician to program stimulation therapy for patient 18, e.g., using input keys and a display. Using programmer 19, for example, the physician may specify the stimulation parameters, such as the voltage or current amplitude, width, and rate of the stimulation pulses. Programmer 19 supports radio frequency telemetry with device 12 to upload stimulation parameters and, optionally, to download operational or physiological data stored by device 12. In this manner, the programmer 19 may be use to periodically interrogate device 12 for purposes of evaluation and, if necessary, modification of the stimulation parameters.

As mentioned, programmer 19 may also comprise a patient programmer, which would comprise a handheld computing device with more limited programming capacities. In that case, programmer 19 provides patient 8 with an interface for control of stimulation therapy by device 12. For example, patient 8 may use programmer 19 to start, stop or adjust stimulation therapy to an extent deemed acceptable by the physician. In particular, programmer 19 may permit patient 8 to adjust stimulation parameters such as duration, amplitude, pulse width and pulse rate, within an adjustment range set by the physician.

Device 12 and programmer 19 may communicate via wireless communication with using RF telemetry techniques known in the art. Device 12 and programmer 19 may also communicate with each other using any of a variety of local wireless communication techniques, such as RF communication according to the 802.11 or Bluetooth specification sets, or other standard or proprietary telemetry protocols. Numerous other wireless protocols or standards may be used, including wireless techniques, or techniques that use the flesh of patient 8 as the transmission medium.

As mentioned above, the techniques described herein can be used to provide electrical stimulation to the prostate gland in order to treat sexual dysfunction, such as by causing or preventing erection or causing or preventing ejaculation. Alternatively, techniques described herein may be used to treat benign prostatic hyperplasia (BPH), or other urological or prostate disorders. Different types of stimulation or stimulation sequences may be used, depending on the disorder being treated. Also, the electrode placement adjacent the prostate gland may be selected by the physician based on the disorder being treated.

For example, for sexual dysfunction, one or more electrodes may be positioned on or within the cellular or muscular tissue of the prostate gland, possibly close to the corpus cavernosa nerve, which is the nerve that attaches to the surface of the prostate gland. By way of example, the pulses for treating sexual dysfunction may define pulse widths between approximately 10 and 5000 microseconds, more preferably between approximately 100 and 1000 microseconds and still more preferably between 180 and 450 microseconds. The pulses may define amplitudes between approximately 0.1 and 50 volts, more preferably between approximately 0.5 and 20 volts and still more preferably between approximately 1 and 10 volts. The pulses may define frequencies between approximately 0.5 and 500 hertz, more preferably between approximately 10 and 250 hertz and still more preferably between approximately 50 and 100 hertz. The pulses may be AC pulses or DC pulses, and may be mono-phsic, bi-phasic, or multiphasic in various embodiments.

The pulse sequence provided for treating sexual dysfunction may define a substantially continuous pulse sequence that regulates the patient's nervous system near the prostate gland. Alternatively, pulses may be delivered in response to patient programming, e.g., to cause erection or ejaculation during times of intimacy when the patient desires such physiological effects.

In order to treat BPH or other urological or prostate disorders, one or more electrodes may be positioned on or within the tissue of the prostate gland at locations where residual stimulation of the nervous system would be minimized. A wide variety of locations adjacent the prostate gland, however, may also prove effective for treating BPH or other urological or prostate disorders.

In one specific example, the pulse sequence for treating BPH may define a training sequence of therapeutic stimulation pulses which are specifically selected to train the prostate gland. The training may be analogous training used in Cardiomyoplasty. However, unlike Cardiomyoplasty, in which implanted muscle fibers are trained to become contractive, the training of the prostate gland should cause the fibrous cells to relax in order to cause the prostate gland to become more compliant.

For BPH treatment, by way of example, the pulses may define pulse widths between approximately 10 and 500 microseconds, amplitudes less than approximately 10.5 volts, frequencies between approximately 2 and 20 hertz, and pulse intervals between approximately 10 and 500 milliseconds. The pulses may be delivered for different time periods over the coarse of a day. The pulses may be AC pulses or DC pulses, and may be mono-phsic, bi-phasic, or multi-phasic in various embodiments. The training sequence may define a plurality of pulse trains, which increase in frequency of the pulse delivery over the coarse of a plurality of time frames. For example, the sequence may define a first pulse train for delivery during a first week, and a second pulse train for delivery during a second week, a third pulse train for delivery during a third week, and so forth. The second pulse train includes more pulses per unit time than the first pulse train. With each time frame, e.g., each passing week, the pulses per unit time may increase. In this manner, the prostate gland can be trained to become more compliant by relaxing the fiber structure of the prostate gland.

Electrode placement when treating BPH may also be done cognizant of potential sexual side effects. In particular, the training sequence may be delivered without causing sexual stimulation, e.g., by ensuring proper electrode placement at locations that are not in close proximity to various prostate nerves such as the corpus cavernosa nerve.

Figure 2:
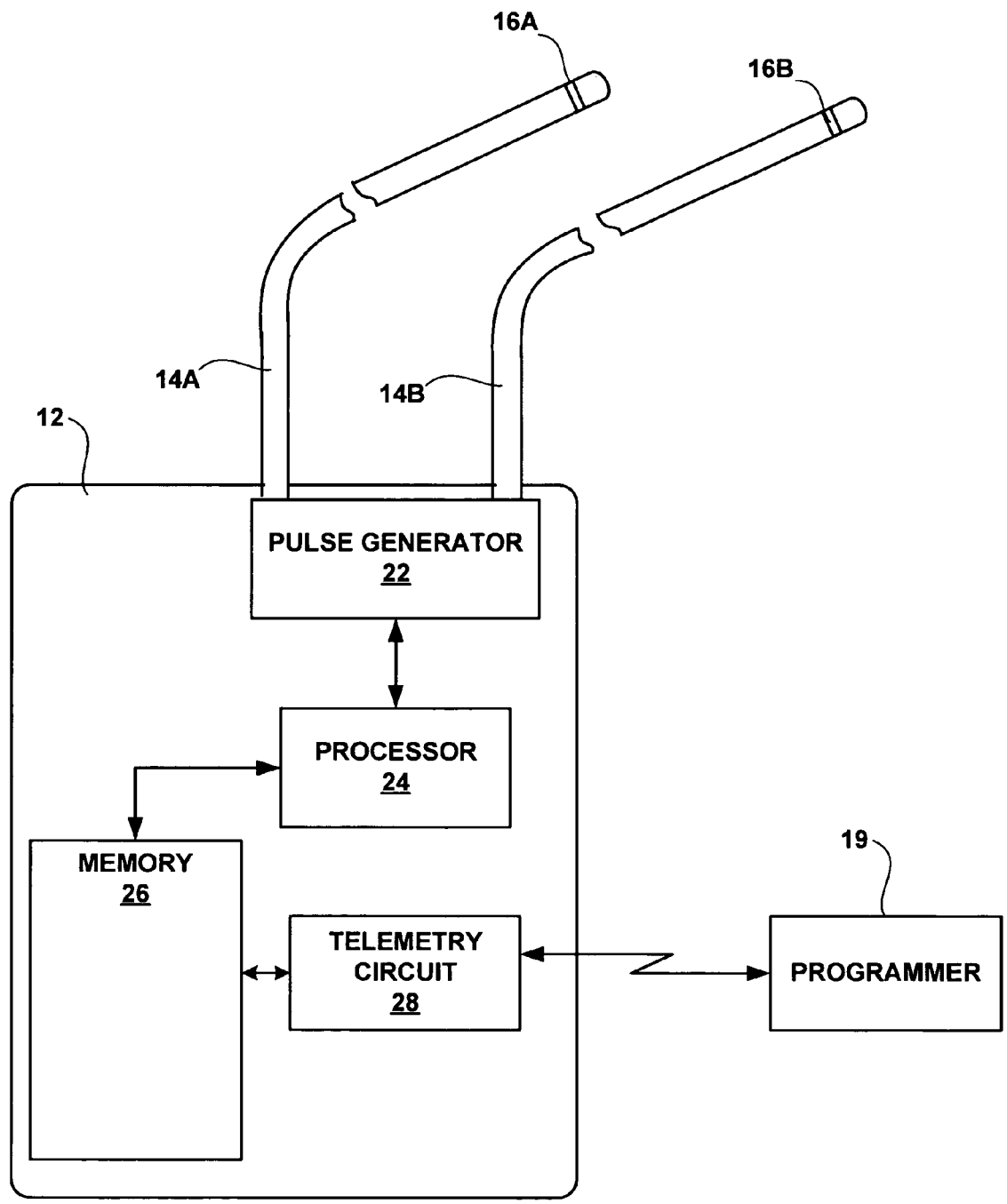
FIG. 2 is a block diagram illustrating an exemplary implantable medical device that can perform one or more of the techniques described herein.

FIG. 2 is a block diagram illustrating an exemplary implantable medical device 12 in greater detail. Device 12 delivers stimulation therapy to a patient's prostate gland via electrodes 16A, 16B of leads 14A, 14B. Electrodes 16 may be ring electrodes, although the invention is not limited in that respect. Moreover any number of leads, and any number of electrodes may be used. In the illustrated example of FIG. 2, leads 14 are monopolar leads, however, any number of electrodes may be deposed on a give lead. A single lead could also be used in accordance with the invention.

Electrodes 16 are electrically coupled to a pulse generator 22 of implantable medical device 12 via leads 14. Pulse generator 22, for example, may include one or more capacitors that charge from a power source, such as a battery. Pulse generator 22 may also include timing circuitry to cause discharge of the capacitors and thereby cause electrical stimulation pulses to be delivered to electrodes 16 at selected times.

Processor 24 controls the timing of pulse delivery, e.g., by sending commands to the timing circuitry of pulse generator 22. In particular, Processor 24 controls pulse generator 22 to cause delivery of stimulation therapy according to selected stimulation parameters. The selected stimulation parameters may be stored in memory 26, and may be modified or updated via communication from programmer 19 to telemetry circuit 28. Specifically, memory 26 can be loaded with selected amplitudes, pulse widths, and rates specified by the programs communicated from programmer 19 to telemetry circuit 28. Processor 24 accesses the parameters and programs in memory 26 for execution in order to control pulse generator 22. Processor 24 may include a microprocessor, a controller, a digital signal processor (DSP), an application specific integrated circuit (ASIC), a field programmable gate array (FPGA), discrete logic circuitry, or the like.

In some embodiments, memory 26 stores multiple sets of stimulation parameters that are available to be selected by the patient or physician. As described herein, the stimulation parameters may be formulated for treatment of sexual dysfunction, or prostate or urological disorders such as BPH. The stimulation parameters may also be defined to alleviate pain, or other symptoms associated with prostate disorders.

Memory 26 also stores program instructions that, when executed by processor 24, cause device 12 to deliver stimulation therapy. Memory 26 may include any volatile or non-volatile media, such as a RAM, ROM, CD-ROM, NVRAM, EEPROM, flash memory, and the like. Accordingly, the invention also contemplates computer-readable media storing instructions to cause processor 24 to provide the functionality described herein.

Telemetry circuit 28 supports wireless communication between device 12 and programmer 19 such as a physician or clinician programmer, a patient programmer, or the like. In addition, in some embodiments, telemetry circuit 28 supports wireless communication with one or more wireless sensors that sense physiological signals and transmit the signals to device 12. In that case, the stimulation therapy may be responsive to sensed conditions.

Figure 3:
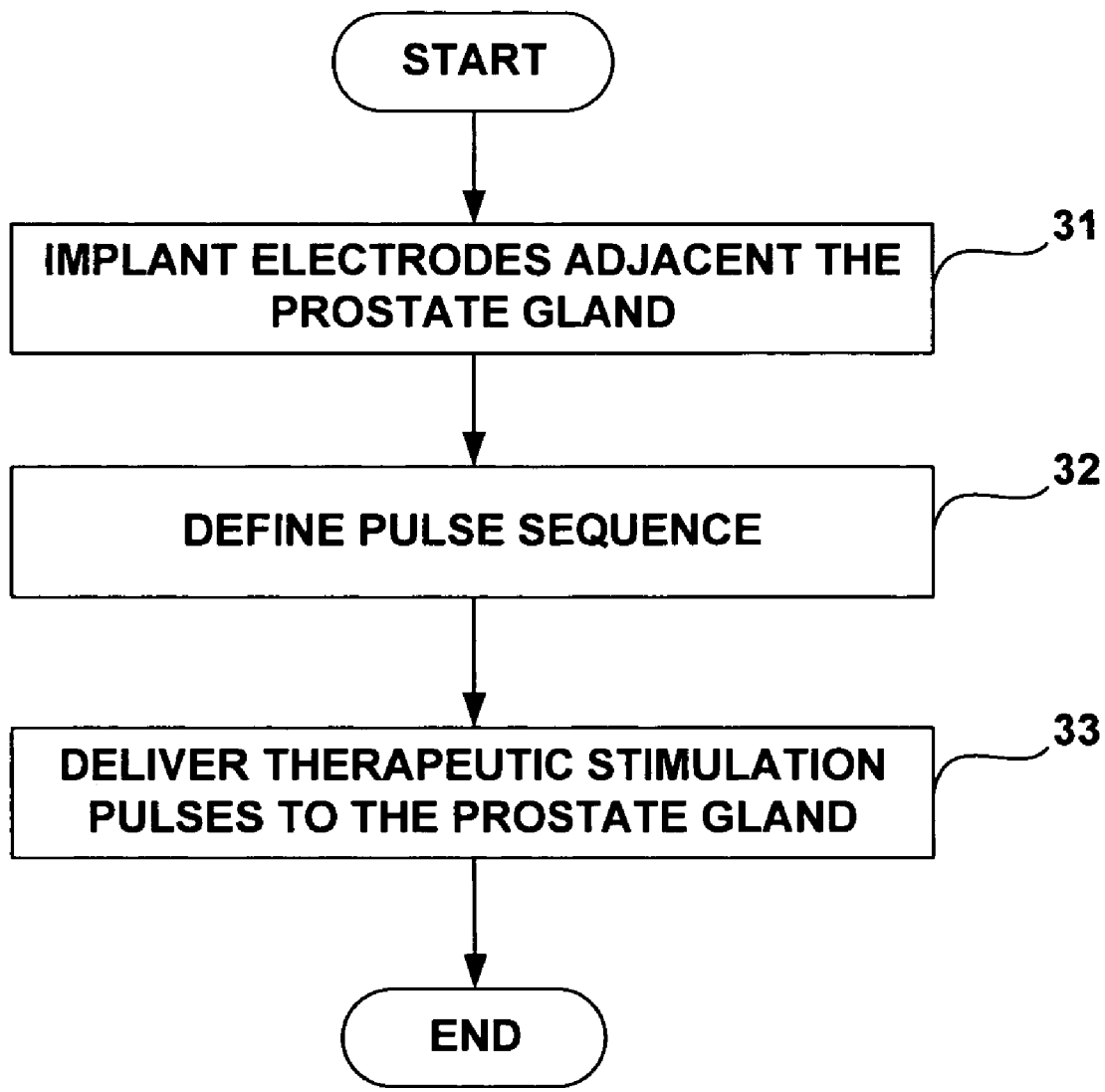
FIG. 3 is a flow diagram illustrating a technique for stimulating the prostate gland according to an embodiment of the invention.

FIG. 3 is a flow diagram illustrating a technique for stimulating the prostate gland according to an embodiment of the invention. As shown, a physician implants electrodes 16 adjacent prostate gland 5 (31). The physician then defines a pulse sequence consistent with the desired therapy (32). In particular, the physician can program device 12 via programmer 19 to load stimulation parameters that can be used by device 12 to control the stimulation therapy. The parameters and simulation may be different for different types of therapeutic prostate stimulation, as described herein. For example, the parameters may be defined to treat sexual dysfunction or alternatively, may be defined to treat BPH. In the later case, the parameters may define a training sequence including a plurality of pulse trains that change over the coarse of time in order to train the prostate gland to relax and become more compliant. Once programmed, implantable medical device 12 delivers therapeutic stimulation pulses to prostate gland consistent with the selected pulse sequence (33). In this manner, implantable medical device 12 can provide therapy to patient 8 by stimulating prostate gland 5.

Again, the parameters programmed into implantable medical device 12 may be defined differently, depending on the type of therapy to be delivered. For sexual dysfunction applications, for example, the parameters may establish pulse widths the pulses for treating sexual dysfunction may define pulse widths between approximately 10 and 5000 microseconds, more preferably between approximately 100 and 1000 microseconds and still more preferably between 180 and 450 microseconds. The pulses may define amplitudes between approximately 0.1 and 50 volts, more preferably between approximately 0.5 and 20 volts and still more preferably between approximately 1 and 10 volts. The pulses may define frequencies between approximately 0.5 and 500 hertz, more preferably between approximately 10 and 250 hertz and still more preferably between approximately 50 and 100 hertz. In that case, the parameters may define a substantially continuous sequence of timed pulses, or may define a sequence that is responsive to patient commands. For example, the patient may use a programmer to initialize a pulse sequence that causes erection or ejaculation during times of intimacy when the patient desires such physiological effects.

Alternatively, the parameters may establish different pulse characteristics for BPH treatment. For BPH applications, for example, the parameters may establish pulse widths between approximately 10 and 500 microseconds, amplitudes less than approximately 10.5 volts, frequencies between approximately 2 and 20 hertz, and pulse intervals between approximately 10 and 500 milliseconds. In addition, for BPH, the parameters may define a training sequence including a plurality of pulse trains that change over the coarse of time in order to train the prostate gland to relax and become more compliant.

Figure 4:
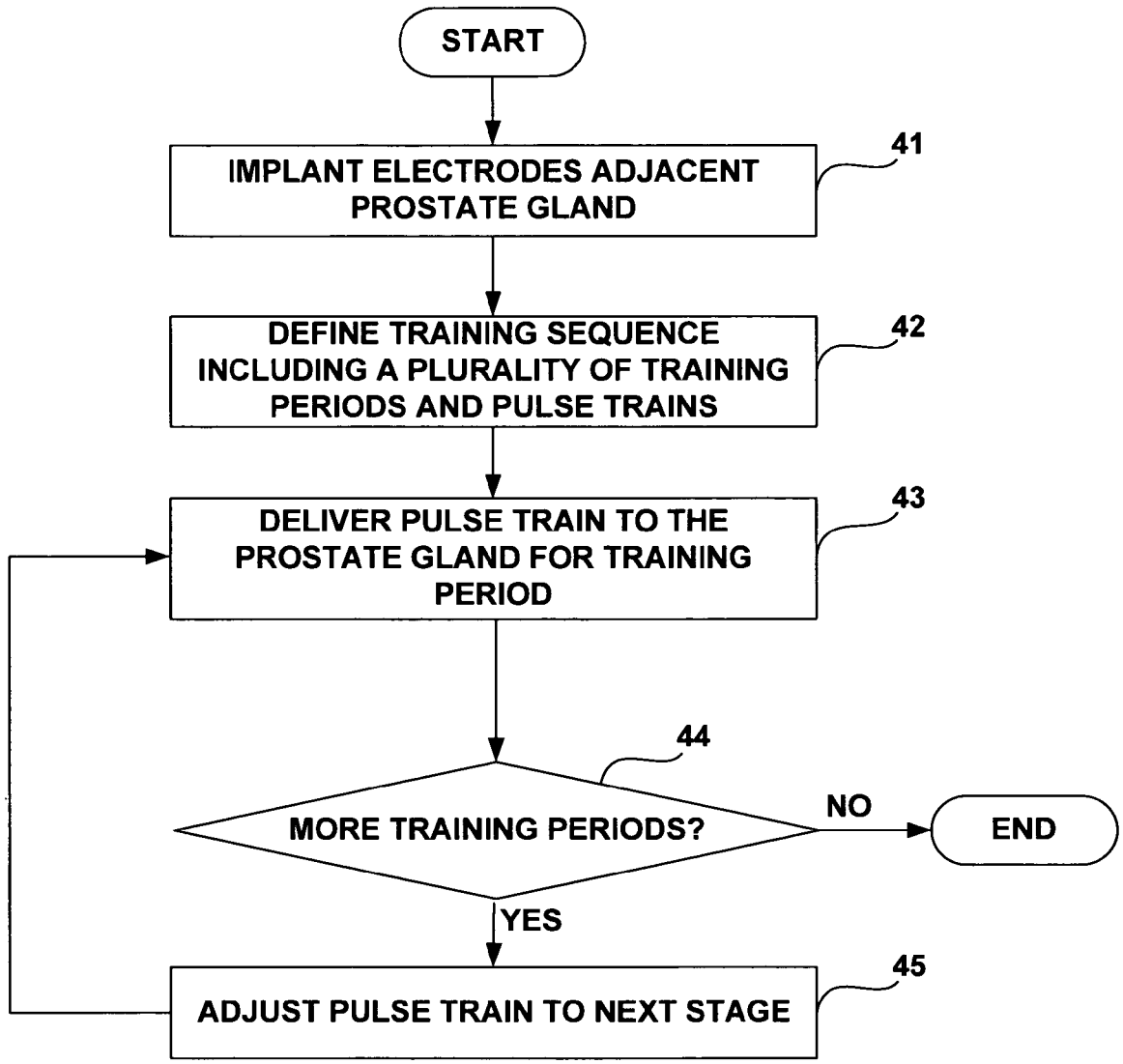
FIG. 4 is a flow diagram illustrating a technique for stimulating the prostate gland in order to train the prostate gland and change the fiber structure of the prostate gland.

FIG. 4 is a flow diagram illustrating a technique for stimulating the prostate gland in order to train the prostate gland and change the fiber structure of the prostate gland. As shown in FIG. 4, a physician implants electrodes 16 adjacent prostate gland 5 (41). The physician then defines a training sequence of stimulation pulses that define a plurality of training periods and a plurality of pulse trains (42).

In particular, the physician can program device 12 via programmer 19 to load stimulation parameters that can be used by device 12 to control the stimulation therapy. For treatment of BPH, the parameters may establish stimulation settings as described herein. In addition, for treatment of BPH, the parameters may define a training sequence including a plurality of pulse trains that change over the coarse of time in order to train the prostate gland to relax and become more compliant. In particular the parameters may establish a first training period and a first pulse rate, a second training period and a second pulse rate, a third training period and a third pulse rate, a fourth training time period and a fourth pulse rate, and so forth.

Device 12 delivers a pulse train to the prostate gland for the first training period (43). In particular, device 12 delivers a pulse train to the prostate gland defined by the first pulse rate for period of time corresponding to the first training period. The first training period may be on the order of one week, although the invention is not limited in that respect.

If there are more training periods (yes branch of 44), implantable medical device adjusts the pulse train to the next stage (45). Device 12 then delivers the next pulse train to the prostate gland (43). In particular, at this point, device 12 delivers a pulse train to the prostate gland defined by the second pulse rate for period of time corresponding to the second training period. The second training period may also be on the order of one week, although the invention is not limited in that respect. The second pulse rate may be a higher rate than the first pulse rate.

If there are more training periods (yes branch of 44), implantable medical device adjusts the pulse train to the next stage (45). Device 12 then delivers the next pulse train to the prostate gland (43). In particular, at this point, device 12 delivers a pulse train to the prostate gland defined by the third pulse rate for period of time corresponding to the third training period. The third training period may also be on the order of one week, although the invention is not limited in that respect. The third pulse rate may be a higher rate than the second pulse rate.

This process may continue for any number of training periods, with the pulse rate increasing with each subsequent period. The number of training periods may be defined by the stimulation parameters programmed into implantable medical device 12 using programmer 19. The delivery of pulse trains to the prostate gland in an increasing fashion over the course of a number of training periods can train the prostate gland to be more compliant, e.g., by changing the fiber structure of the prostate gland. In this manner, device 12 can provide treatment for BPH. In additional embodiments, other pulse parameters may be changed in the different training periods. For example, it may be desirable not only to modify the rate, but also to modify the pulse widths, amplitudes, frequencies, or durations of the given pulses for each training period.

Figure 5:
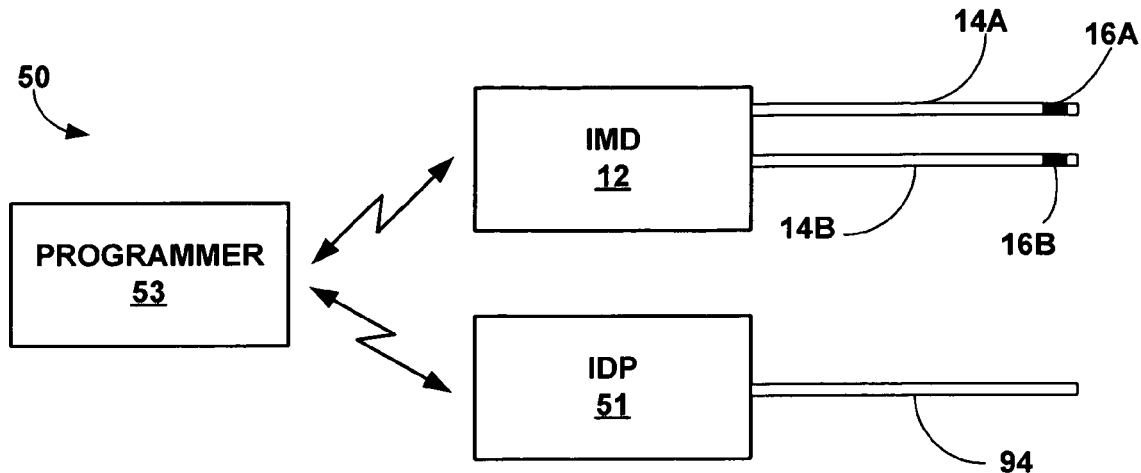
FIG. 5 is a block diagram illustrating an implantable system for delivery of drug therapy and delivery of stimulation therapy to the prostate gland of a patient.

FIG. 5 is a block diagram illustrating an implantable system 50 for delivery a drug and delivery of stimulation to the prostate gland of a patient. As shown in FIG. 5, system 50 includes an implantable medical device 12, substantially similar to that described above. In particular, implantable medical device 12 includes one or more leads 14 with one or more electrodes 16 that deliver stimulation therapy to a patient's prostate gland as described herein. In addition, system 50 includes an implantable drug pump (IDP) 51. Optionally, system 50 may include a programmer 53 that controls both drug pump 51 and implantable medical device 12. IDP 51 could be eliminated in favor of a different agent pump that delivered biological or genetic agents, rather than pharmaceutical drugs.

Implantable drug pump 51 includes an implantable drug delivery catheter 94. System 50 generally performs the functions of system 12 of FIG. 1, in the sense that system 50 treats sexual dysfunction or prostate disorders via prostate stimulation. However, system 50 further augments the stimulation of the prostate gland with drug therapy from implantable drug pump 51. The stimulation from implantable medical device 12 may be delivered before, after, or simultaneous with drug deliver by implantable drug pump 51. Implantable drug pump 51, for example, my deliver drugs to the prostate gland to compliment the delivery of simulation pulses to the prostate gland. In that case, stimulation may trigger the drugs, or the drugs may improve the affect of the stimulation.

The invention is not limited to the types of drugs delivered to the prostate gland via implantable drug pump 51 for complimentary therapy with implantable medical device 12. In some cases, implantable drug pump 51 could be eliminated in favor of another type of medical pump that delivers any agent, including conventional drugs, or possibly genetic or other biological materials. In other words, implantable drug pump 51 is not meant to be limiting of the invention. The device may delivery pharmaceutical drugs, biological materials, genetic materials or any other agent or material that may aid or augment the simulation of the prostate gland.

In an alternative embodiment, an implantable medical device may incorporate an agent pump, such as an implantable drug pump. In other words, an implantable stimulator and an implantable agent or drug pump may be integrated into a single device to provide a combination of therapy to the prostate gland tissue. In that case, the implantable medical device would both stimulate the tissue of the prostate gland and provide agent therapy to the prostate gland such as drug therapy, gene therapy, or other biological therapy. The device would be similar to IMD 12 (FIG. 5), with IDP 51 housed inside IMD 12. In that case, for example, the device may include a stimulator and an IDP integrated into a common implantable housing. The stimulator and agent pump may be programmed, as described herein, to deliver the stimulation pulses and the agents to the prostate gland in a complimentary fashion. For example the stimulation pulses may define a training sequence which in conjunction with the agents, causes a fiber structure of the prostate gland to change.

Figure 6:
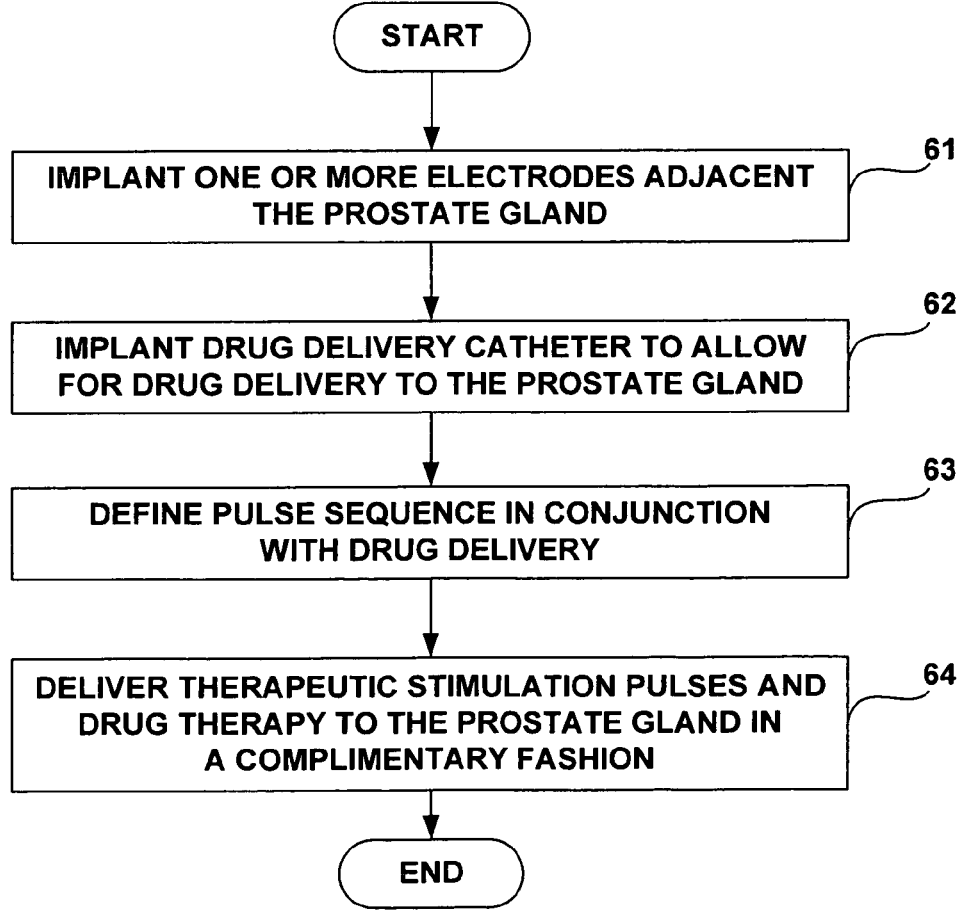
FIG. 6 is a flow diagram illustrating operation of the system of FIG. 5.

FIG. 6 is a flow diagram illustrating operation of system 50 of FIG. 5. As shown in FIG. 6, the method involves implanting one or more electrodes adjacent to the prostate gland (61) and implanting a drug delivery catheter to allow for drug delivery to the prostate gland (62). The physician then defines a pulse sequence in conjunction with the drug therapy (63). In particular, the physician can program implantable medical device 12 and implantable drug pump 51 via programmer 53 to load stimulation parameters that can be used by device 12 to control the stimulation therapy and timing and dosage parameters that can be used by implantable drug pump 51. The parameters may be different for different types of therapeutic prostate stimulation. For example, the parameters may be defined to treat sexual dysfunction or alternatively, may be defined to treat BPH. As described above, the parameters may define a training sequence including a plurality of pulse trains that change over the course of time in order to train the prostate gland to relax and become more compliant. However, in this case, drug therapy may further augment the prostate training for improved results. Again, gene therapy or the like, could also be used.

Once programmed, implantable medical device 12 delivers therapeutic stimulation pulses to prostate gland in a complimentary fashion with the delivery of drugs from implantable drug pump 51 (64). In this manner, system 50 can provide therapy to a patient by both stimulating prostate gland and providing drug therapy to the prostate gland. Again, such complimentary therapy includes stimulation from implantable medical device 12 before, after, or simultaneous with drug deliver by implantable drug pump 51.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using devices and systems for delivery of a denervating agent, as described herein. As used herein, the term patient refers to any animal that includes a prostate gland, i.e. male animals. Put another way, the same techniques and devices described herein may also be useful for human or non-human patients.

In the appended claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A method of providing medical therapy to a patient, the method comprising delivering a training sequence of stimulation pulses to a prostate gland via an implantable medical device, wherein the implantable medical device includes one or more electrodes that are deployed on or implanted within cellular muscle tissue of the prostate gland, the training sequence being defined to change a fiber structure of the prostate gland, wherein the training sequence defines a first pulse train and a second pulse train, wherein the first pulse train and the second pulse train are each delivered over time periods on an order of a week, the second pulse train being delivered after the first pulse train, wherein the second pulse train includes more pulses per unit time than the first pulse train.

2. The method of claim 1, further comprising delivering the training sequence to relax the fiber structure of the prostate gland.

3. The method of claim 1, wherein the pulses define pulse widths between approximately 10 and 500 microseconds, amplitudes less than approximately 10.5 volts, frequencies between approximately 2 and 20 hertz, and pulse intervals between approximately 10 and 500 milliseconds.

4. The method of claim 1, further comprising delivering drugs to the prostate gland in conjunction with delivering the one or more therapeutic stimulation pulses.

5. An implantable medical device comprising:
   means for generating a training sequence of therapeutic stimulation pulses;
   means for delivering the training sequence of therapeutic stimulation pulses to a prostate gland such that the training sequence of therapeutic stimulation pulses cause a fiber structure of the prostate gland to change, wherein the training sequence defines a first pulse train and a second pulse train, wherein the first pulse train and the second pulse train are each delivered over time periods on an order of a week, the second pulse train being delivered after the first pulse train, wherein the second pulse train includes more pulses per unit time than the first pulse train, wherein means for delivering the training sequence includes one or more electrodes that are deployed on or implanted within cellular muscle tissue of the prostate gland.

6. The implantable medical device of claim 5, wherein the training sequence of therapeutic stimulation pulses cause the fiber structure of the prostate gland to relax.

7. A method of providing medical therapy to a patient, the method comprising:
   delivering a first pulse train to a prostate gland over a first period of time; and
   delivering a second pulse train to the prostate gland over a second period of time, wherein the second pulse train is different than the first pulse train, and wherein delivering the first and second pulse trains causes a fiber structure of the prostate gland to change, wherein the first pulse train and the second pulse train are each delivered over time periods on an order of a week, wherein the first and second pulse trains are delivered via one or more electrodes deployed on or implanted within cellular muscle tissue of the prostate gland.

8. The method of claim 7, wherein the second pulse train defines a pulse rate that is higher than that of the first pulse train.

9. The method of claim 7, further comprising delivering a third pulse train to the prostate gland over a third period of time, wherein the third pulse train is different than the first or second pulse train, and wherein delivering the first, second and third pulse trains causes a fiber structure of the prostate gland to change.

10. The method of claim 9, further comprising delivering a fourth pulse train to the prostate gland over a fourth period of time, wherein the fourth pulse train is different than the first, second or third pulse train, and wherein delivering the first, second, third and fourth pulse trains causes a fiber structure of the prostate gland to change.

11. The method of claim 10, wherein the fourth pulse train defines a fourth pulse rate that is higher than that of the third pulse train, the third pulse train defines a third pulse rate that is higher than that of the second pulse train and the second pulse train defines a second pulse rate that is higher than that of the first pulse train.

12. An implantable medical device comprising:
   one or more leads including one or more electrodes for implantation adjacent a prostate gland within cellular muscle tissue of the prostate gland;
   a pulse generator to generate therapeutic stimulation pulses and deliver the pulses to the one or more electrodes via the one or more leads; and
   a processor configured to control the therapy delivery circuit such that the therapeutic stimulation pulses define a training sequence which causes a fiber structure of the prostate gland to change, wherein the training sequence defines a first pulse train and a second pulse train, wherein the first pulse train and the second pulse train are each delivered over time periods on an order of a week, the second pulse train being delivered after the first pulse train, wherein the second pulse train includes more pulses per unit time than the first pulse train.

13. The implantable medical device of claim 12, wherein the training sequence causes the fiber structure of the prostate gland to relax.

14. The implantable medical device of claim 12, wherein the pulses define pulse widths between approximately 10 and 500 microseconds, amplitudes less than approximately 10.5 volts, frequencies between approximately 2 and 20 hertz, and pulse intervals between approximately 10 and 500 milliseconds.

* * * * *